US010041059B2

(12) United States Patent
Klinkenberg et al.

(10) Patent No.: US 10,041,059 B2
(45) Date of Patent: Aug. 7, 2018

(54) METHODS FOR THE PREPARATION OF HYDROGELS

(71) Applicant: SPERMVITAL AS, Hamar (NO)

(72) Inventors: Geir Klinkenberg, Heimdal (NO); Kjell Domaas Josefsen, Trondheim (NO); Elisabeth Kommisrud, Stange (NO)

(73) Assignee: SPERMVITAL AS, Hamar (NO)

( * ) Notice: Subject to any disclaimer, the term of this patent is extended or adjusted under 35 U.S.C. 154(b) by 0 days.

(21) Appl. No.: 15/406,936

(22) Filed: Jan. 16, 2017

(65) Prior Publication Data

US 2017/0121700 A1    May 4, 2017

Related U.S. Application Data

(62) Division of application No. 14/360,102, filed as application No. PCT/EP2012/073434 on Nov. 23, 2012, now Pat. No. 9,578,871.

(60) Provisional application No. 61/563,550, filed on Nov. 24, 2011.

(30) Foreign Application Priority Data

Nov. 24, 2011  (GB) .................................. 1120368.4

(51) Int. Cl.
| | |
|---|---|
| *A01N 1/02* | (2006.01) |
| *C12N 11/04* | (2006.01) |
| *C12P 19/04* | (2006.01) |
| *C12N 9/20* | (2006.01) |
| *C12N 11/10* | (2006.01) |
| *C12N 9/14* | (2006.01) |

(52) U.S. Cl.
CPC ............ *C12N 11/04* (2013.01); *A01N 1/0231* (2013.01); *C12N 9/14* (2013.01); *C12N 9/20* (2013.01); *C12N 11/10* (2013.01); *C12P 19/04* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,695,463 | A | 9/1987 | Yang et al. |
| 4,990,601 | A | 2/1991 | Skjak-Braek et al. |
| 5,639,467 | A | 6/1997 | Dorian et al. |
| 6,656,508 | B2 | 12/2003 | Goldenberg et al. |
| 2006/0159823 | A1 | 7/2006 | Melvik et al. |
| 2014/0302484 | A1 | 10/2014 | Klinkenberg et al. |

FOREIGN PATENT DOCUMENTS

| | | |
|---|---|---|
| WO | 198603781 A1 | 7/1986 |
| WO | 199846211 A1 | 10/1998 |
| WO | 200140370 A2 | 6/2001 |
| WO | 2006028996 A2 | 3/2006 |
| WO | 2006106400 A2 | 10/2006 |
| WO | 2008004890 A2 | 1/2008 |

OTHER PUBLICATIONS

Ferrer, Pau, and Carles Solà. "Lipase production by immobilized Candida rugosa cells." Applied microbiology and biotechnology 37.6 (1992): 737-741. (Year: 1992).*
Lotti, Marina, et al. "Physiological control on the expression and secretion of Candida rugosa lipase." Chemistry and physics of lipids 93.1 (1998): 143-148. (Year: 1998).*
Betigeri, et al.; "Immobilization of Lipase Using Hydrophilic Polymers in the Form of Hydrogel Beads"; Biomaterials; 23; pp. 36-27-3636; (2002).
CN101439206 A; published May 27, 2009 Abstract only.
Hertzberg et al.; "Alginate as Immobilization Matrix and Stabilizing Agent in a Two-phase Liquid System: Application in Lipase-catalysed Reactions"; Enzyme and Microbial Technology, Stoneham, MA, US, 14(1); pp. 42-47; (1992).
Hertzberg et al.; "Alginate as Immobilization Matrix and Stabilizing Agent in a Two-phase Liquid System: Application in Lipase-catalysed Reactions"; Enzyme Microb. Technol; 14; pp. 42-47 (1992).
International Search Report and Written Opinion; International Application No. PCT/EP2012/073434; Internatioinal Filing Date Nov. 23, 2012; dated May 6, 2013; 13 pages.
JP 2014-542843, First Office Action with English Abstract, drafting date Jun. 13, 2016; dated Jun. 22, 2016; Mailing No. 269267; 9 pages.
JP2009114449 A, May 28, 2009; Applicant Kraft Foods Global Brands LLC; with English Abstract; 39 pages.
JPH07136240 A; May 30, 1995, Applicant: Kuraray Co.; with English Abstract; 7 pages.
JPH07155369 A, Jun. 20, 1995; Applicant Mitsubishi Plastics Inc; with English Abstract; 4 pages.
JPH09176021 A, Jul. 8, 1997, Applicant: Takaya et al; Nisshin Spinning; With Engilsh Abstract; 12 pages.
Liu et al.; "Glucose Oxidase-Mediated Gelation: A Simple Test to Detect Glucose in Food Products"; Journal of Agricultural and Food Chemistry; 60(36) pp. 8963-8967; (2012).
Liu et al.; "Immobilization and Bioactivity of Glucose Oxidase in Hydrogel Microspheres Formulated by an Emulsification—internal Gelation-adsorption-polyelectrolyte Coating Method"; International Journal of Pharmaceutics; 339; pp. 148-156; (2007).
Poncelet et al.; "Production of Alginate Beads by Emulsification/Internal Gelation. I. Methodology"; Applied Microbiology and Biotechnology, Springer, Berlin, DE; 38; pp. 39-45; (1992).
Sawangpanya, et al.; "Immobilization of Lipase on CaCO3 and Entrapment in Calcium Alginate Bead for Biodiesel Production"; Science Journal Ubon Ratchathani University, 1; pp. 46-51; (2010).
Smidsrod et al; "Alginate as Immobilization Matrix for Cells"; Trends in Biotechnology; 8; pp. 71-78; (1990).
Wang et al.; Injectable Biodegradable Hydrogels with Tunable Mechanical Properties for the Stimulation of Neurogenesic Differentiation of Human Mesenchymal Stem Cells in 3D Culture; Biomaterials; 31; pp. 1148-1157; (2010).
Westhaus et al.; "Triggered Release of Calcium from Lipid Vesicles: a Bioinspired Strategy for Rapid Gelation of Polysaccharide and Protein Hydrogels"; Biomaterials; 22; pp. 453-462; (2001).
Wu et al.; "Kinetics of Tributyrin Hydrolysis by Lipase"; Enzyme and Microbial Technology; 35; pp. 488-493; (2004).

* cited by examiner

*Primary Examiner* — Robert J Yamasaki

(74) *Attorney, Agent, or Firm* — Cantor Colburn LLP

(57) ABSTRACT

The present invention relates to an improved method for preparing hydrogels, such as alginate hydrogels. The hydrogels of the present invention is in particular useful for immobilization and preservation of biological material, such as cellular material, e.g. spermatozoa.

1 Claim, No Drawings

METHODS FOR THE PREPARATION OF HYDROGELS

CROSS-REFERENCE TO RELATED APPLICATIONS

This application is a divisional of U.S. application Ser. No. 14/360,102, filed May 22, 2014, which is a 371 of PCT/EP2012/073434 filed on Nov. 23, 2012, which claims the benefit of priority to U.S. provisional application No. 61/563,550 filed on Nov. 24, 2011 and to United Kingdom Application No. 1120368.4 filed on Nov. 24, 2011, under the provisions of 35 U.S.C. 119 and the International Convention for the protection of Industrial Property, which are incorporated herein by reference

FIELD OF THE INVENTION

The present invention relates to an improved method for preparing hydrogels, in particular alginate hydrogels. The hydrogels of the present invention have a wide area of application and are in particular useful for immobilisation of biological material, more particularly for the immobilisation and preservation of cellular material, such as e.g. spermatozoa.

BACKGROUND OF THE INVENTION

Hydrogels consist of polymer chains forming a hydrophilic, water containing network having a wide area of application within various industrial fields, in particular within the biotechnological and pharmaceutical industry. For example, hydrogels are used to immobilize biological material such as cells for transplantation or as delivery system for e.g. pharmaceutical active ingredients or nutrients. Hydrogels may also be useful as wound dressings. Furthermore, hydrogels, in particular alginate hydrogels, is widely used as thickening agents.

A widely used polymer for the formation of hydrogels is alginate. Alginate are naturally occurring, anionic polysaccharides consisting of 1,4-linked-β-D-mannuronic acid (M) and α-L-glucuronic acid (G). (Smidsrød and Skjåk-Bræk, 1990, Trends in biotechnology, vol. 8, no. 3, pp 71-78). Commercial alginates are extracted from seaweed, such as *Ascophyllum nodosum, Macrocystis pyrifera,* and *Laminaria hyperborea,* and also to some extent *Laminaria digitata, Laminaria japonica, Eclonia maxima, Lesonia negrescens* and *Sargassum* sp.

Alginates may also be prepared from some alginate producing bacteria, e.g. from some *Pseudomonas* species and from *Azotobacter vinelandii* (Smidsrød and Skjåk-Bræk, 1990, supra).

Alginates are commonly used inter alia in the food industry, e.g. as stabilizers for viscosity control, or as thickening agents. Alginates are also widely used within the pharmaceutical industry and cosmetic industry, also as stabilizers, thickening agent or disintegrant. For the various purposes, alginates being rich in either guluronic acid or mannuronic acid, respectively, are available (Mancini et al. (1999), Journal of Food Engineering 39, 369-378, WO8603781, U.S. Pat. No. 4,990,601, U.S. Pat. No. 5,639, 467).

Due to alginates biocompatibility and ability to gel in presence of divalent cations such as e.g. calcium ions, alginate is also commonly used for encapsulation of cells (Nebel, R. L., Balme, J., Saacke, R. G. and Lim. F. (1985), J. Anim. Sci. 60:1631-1639, Lim, F and Sun, A. M., (1980) Science 210: 908-9100, WO 2006/106400, EP0922451, U.S. Pat. No. 6,596,310, Torre et al. (1998), S.T.P. Pharma Sciences, 8 (4), pp. 233-236, Torre et al., (2000), Biomaterials, 21, pp. 1493-1498, Torre et al. (2002), Journal of Controlled Release, 85, pp. 83-89, Faustini et al, (2004), Theriogenology, 61, 173-184, Weber et al. (2006), Journal of Biotechnology, 123, pp. 155-163.

Alginate gels are also useful for immobilising various materials. For example, WO2008/004890 describes biopolymer particles useful for preservation of spermatozoa, and wherein the biological material is embedded in a polymer particle being solid throughout the whole diameter of the particle. By embedding the spermatozoa in the alginate hydrogels instead of encapsulating the spermatozoa, leaving the spermatozoa in the fluid core of the capsules, the cells are immobilized within the alginate gel network, so restricting the motility of the cells during storage.

Alginate hydrogels, e.g. alginate gels used for encapsulation or entrapment of various materials, may be prepared by mixing a solution of the material to be entrapped with a sodium alginate solution, and adding this solution into a solution containing multivalent cations, usually divalent cations such as calcium ions (e.g. a solution of $CaCl_2$) (Smidsrød and Skjåk-Bræk, 1990, supra).

U.S. Pat. No. 6,497,902 disclose another method for preparing biocompatible hydrogels, such as alginate hydrogels, comprising mixing the cells to be embedded, alginate salt and a calcium releasing agent, and thereafter adding a calcium releasing compound to said mixture to form a cross-linked gel. According to U.S. Pat. No. 6,497,902, the calcium releasing agent may be D-glucono-δ-lactone (GDL).

The method disclosed in U.S. Pat. No. 6,497,902 may be used to immobilize spermatozoa useful for artificial insemination (e.g. for the preparation of alginate hydrogels disclosed in WO 2008/004890). For example, diluted and cooled (4° C.) spermatozoa may be added to a solution comprising dissolved sodium alginate and suspended calcium carbonate, and optionally a cryoprotectant such as glycerol, and thereafter initiating gelling and obtaining the desired alginate hydrogel by adding a solution comprising GDL. The addition of the GDL results in the formation of gluconic acid which in turn will react with water and form $H_3O^+$. The increase in $H_3O^+$, and the presence of calcium carbonate, results in the release of $CO_2$ and $Ca^{2+}$. The providing of $Ca^{2+}$ by the adding the GDL results in formation of the alginate hydrogel with embedded spermatozoa.

After gelling has occurred, the containers filled with spermatozoa embedded in alginate may be cryopreserved in liquid nitrogen, thus providing cryopreservation of spermatozoa having exceptionally long shelf life.

However, the present inventors have experience that the use of GDL in preparing alginate hydrogels according to the method disclosed in U.S. Pat. No. 6,497,902 involves several drawbacks. When preparing alginate gel comprising immobilized spermatozoa according to the method described above, it is vital that GDL is added to the solution immediately after the GDL solution is prepared to avoid spontaneous gelling. GDL must be added in dissolved form rather than as powder to avoid local areas/zones with high concentrations of gluconic acid initially, which would be detrimental to the spermatozoa. Furthermore, after the addition of GDL, a period of increasing viscosity will follow as a result of the initiation of the gelling reaction. Due to the increasing viscosity, the container used to form the hydrogel must be filled rather quickly. During the accrued time for transforming the dissolved GDL to glucuronic acid, the solution is therefore transferred to suitable containers (such as e.g. mini straw provided from IMV, L'Aigle, France) for further gelling and immobilizing of the desired biological material. The method disclosed in the prior art do therefore result in a rather short and inflexible time schedule for preparing the hydrogels comprising the desired biological material and are a substantial disadvantage from an industrial point of view.

Due to the drawbacks of the method described above, there is a need for an improved method for preparing hydrogels, in particular a method being suitable for preparing hydrogels on an industrial scale.

Various other methods for preparing hydrogels have been described in the prior art. Various reports disclose the utilization of enzymes which upon being subjected to a specific substrate provides for various reactions that in the end results in crossbinding of various types of polymers.

For example, CN 101439206 discloses inter alia the use of polymers comprising a phenolic hydroxyl unit and dioxygenase in an enzyme catalyzed process for the preparation of polymer gels.

Johnsen et al. (2010), ACS Applied Materials & Interfaces, 2(7), pp. 1963-1972, report the preparation of PEG based hydrogel being polymerised using glucose oxidase. The glucose oxidase catalyses the oxidation of β-D-glucose, and the subsequent use of oxygen to generate the flavin adenine dinucleotid enzyme cofactor, results in formation of $H_2O_2$. By combining ferrous ions with this enzymatic $H_2O_2$ production, primary hydroxyl radical species are produced that further reacts with the acrylated monomers.

The use of $H_2O_2$ and horse radish peroxidase in preparation of hydrogels have also been reported, c.f. e.g. Kurisawa et al., (2010), J. of Materials Chemistry, 20(26), pp. 5371-5375, Sakai et al, (2009), Biomaterials, 30(20), pp. 3371-3377, Sakai and Kawakami (2006), Acta Biomaterialia, 20017, 3, pp. 495-501, Lee et al. (2009), J. of Controlled Release, 134, pp. 186-193, Wang et al. (2010), Biomaterials, 31, pp. 1148-1157.

Hydrogels prepared by the use of oxidases and $H_2O_2$ are inappropriate for some application since $H_2O_2$ is a strong oxidant.

There is therefore still a need for an improved and simplified process for the preparation of alginate hydrogels, in particular hydrogels suitable for immobilizing biological material.

SUMMARY OF THE INVENTION

The object of the present invention is to provide an improved process for preparing alginate hydrogels that is not attended with the drawbacks of the processes of the prior art.

Another object of the present invention is to provide simplified process for the preparation of alginate hydrogels suitable for immobilizing biological material.

Thus, the invention relates to an alginate hydrogel wherein the gelling thereof is initiated by utilising a hydrolase and a substrate being hydrolysable by the hydrolase resulting in the formation of $H_3O^+$ and subsequent the release of a divalent cation due to the presence of a divalent cation releasing agent.

According to one aspect of the present invention, a process for the preparation of an alginate hydrogel is provided, said process comprising the mixing of a solution comprising a hydrolase with a solution comprising a substrate being hydrolysable by the hydrolase, and wherein the solution comprising the hydrolase or the solution comprising the substrate being hydrolysable by the hydrolase in addition comprises alginate, and a divalent cation releasing compound. Upon mixing of the two solutions, the binding of the substrate to the hydrolase results in hydrolysis of said substrate and the subsequent formation of $H_3O^+$. The production of $H_3O^+$ furthermore result in the release of divalent cation which thus initiate the formation of the hydrogel.

According to one embodiment, the divalent cation releasing compound and the alginate is present in the solution comprising the hydrolase. According to another embodiment, the divalent cation releasing compound and the alginate is present in the solution comprising the said substrate.

Said hydrolase may be an esterase, such as a lipase. According to one embodiment of the invention, the hydrolase used in the process according to the invention is a triacylglycerol lipase.

According to yet another embodiment of the invention, the divalent cation releasing compounds releases divalent cations selected from the group consisting of $Ca^{2+}$, $Ba^{2+}$, and $Sr^{2+}$.

According to another embodiment of the present invention, the divalent cation releasing compound is a calcium releasing compound, such as e.g. calcium carbonate.

According to yet another embodiment of the present invention, the substrate is an ester of an organic acid.

According to yet another embodiment of the present invention, a process is provided comprising the steps of mixing a solution comprising a triacylglycerol lipase with a solution comprising a substrate being hydrolysable by said hydrolase, wherein the substrate is a compound of formula I:

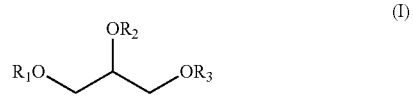

wherein $R_1$, $R_2$, and $R_3$ independently are the same or different and represents a straight or branched, substituted or non-substituted $C_1$-$C_{12}$-alkyl carbonyl chain, and wherein the solution comprising the said lipase or the solution comprising the compound of formula I in addition comprises alginate and a divalent cation releasing compound. According to one embodiment, the $R_1$, $R_2$, and $R_3$ are independently the same or different and represents a straight, non-substituted $C_1$-$C_{12}$-alkyl carbonyl chain, such as a straight, non-substituted $C_1$-$C_3$-alkyl carbonyl chain.

According to yet an embodiment of the present invention, $R_1$, $R_2$, and $R_3$ of formula I are the same of different and represents a straight or branched, substituted or non-substituted $C_1$-$C_3$-alkyl carbonyl chain According to one embodiment of the present invention, $R_1$, $R_2$, and $R_3$ of formula I is selected from the group consisting of methanone, ethanone, acetone, butanone, pentanone, hexanone, heptanone, octanone, nonanone, decanone, or dodecanone.

In particular, e.g. when spermatozoa are to be embedded in the alginate hydrogel, the substrate may be selected from the group consisting of triacetin, tripropionin and tributyrin, preferably tripropionin and tributyrin.

According to another embodiment of the present invention, the solution comprising the hydrolase or the solution comprising substrate being hydrolysable by the hydrolase may in addition comprise an object to be embedded in the alginate hydrogel.

The object to be embedded in the alginate gel may according to one aspect of the invention represent biological material, e.g. cellular material such as spermatozoa.

According to one embodiment of the present invention, a process for preparing alginate hydrogels comprising spermatozoa is provided, wherein the process comprises the steps of i) forming a first solution by diluting spermatozoa with a solution comprising a triacylglycerol lipase;

ii) adding to the first solution obtained in step i), a second solution comprising alginate, a divalent cation releasing compound, and a compound of formula I:

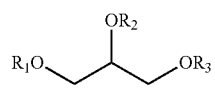

(I)

wherein $R_1$, $R_2$, and $R_3$ independently are the same or different and represents a straight or branched, substituted or non-substituted $C_1$-$C_{12}$-alkyl carbonyl chain, initiating gelling;

iii) transferring the solution obtained in step ii) to a container for gelling of the alginate hydrogel;

iv) optionally subjecting the alginate hydrogel of iii) to cryopreservation.

According to yet another embodiment of the present invention, a process for preparing alginate hydrogels comprising spermatozoa is provided, wherein the process comprises the steps of i) forming a first solution by diluting spermatozoa with a solution comprising a compound of formula I:

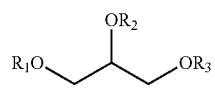

(I)

wherein $R_1$, $R_2$, and $R_3$ independently are the same or different and represents a straight or branched, substituted or non-substituted $C_1$-$C_{12}$-alkyl carbonyl chain;

ii) adding to the solution obtained in step i) a second solution comprising alginate, a divalent cation releasing compound, and a triacylglycerol lipase initiating the gelling;

iii) transferring the solution obtained in ii) to container for gelling of the alginate hydrogel;

iv) optionally subjecting the alginate hydrogel of iii) to cryopreservation.

According to one embodiment, the first and second solution of i) and ii) comprises in addition a cryoprotectant, and the solution obtained in iii) is further subjected to cryoconservation. Furthermore, when preparing alginate hydrogels comprising spermatozoa according to the present invention as outline above, the containers obtained in iii) may furthermore be subjected to cryopreservation, and wherein solution of step i) and/or step ii) comprises a cryoprotectant.

The cryoprotectant present in the solution of step i) and/or step ii) according to this embodiment of the present invention may be selected from the group consisting of glycerol, ethylene glycol, methanol, DMA, DMSO, propylene glycol, trehalose, glucose.

When preparing alginate hydrogels comprising spermatozoa according to the present invention, the divalent cation releasing compound may preferably be calcium carbonate, and the substrate being hydrolysable by the hydrolase may preferably be selected from the group consisting of triacetin, tripropionin and tributyrin.

According to one embodiment of the present invention, the alginate is alginate being rich in guluronic acid.

According to another aspect of the present invention, an alginate hydrogel prepared according to the present invention is provided.

The alginate hydrogel according to the present invention may in one embodiment of the invention comprise:
a. alginate;
b. optionally an object to be embedded in the alginate hydrogel;
c. a hydrolase used in the preparation of the alginate hydrogel.

The alginate hydrogel according to the present invention is formed by gelling of the alginate, and wherein the gelling is achieved by the release of divalent cations from a divalent cation releasing compound as a result of hydrolyse of a hydrolase substrate. The formed hydrogel will thus comprise the hydrolase used in the formation of the gel. The presence of hydrolase in the hydrogel according to the present invention thus indicate that the process of the invention have been applied.

According to another embodiment, the alginate hydrogel according to the invention comprises an embedded object. According to another embodiment, said object to be embedded is a biological material, such as cellular material, e.g. spermatozoa.

According to yet another aspect of the present invention, an alginate hydrogel kit is provided comprising one container comprising a hydrolase and a second container comprising a substrate being hydrolysable by the hydrolase.

One embodiment according to this aspect of the present invention regards an alginate hydrogel kit comprising one container comprising a solution comprising a hydrolase, and a second container comprising a solution comprising alginate, a divalent cation releasing compound and a substrate being hydrolysable by the hydrolase.

Yet another embodiment of this aspect regards an alginate hydrogel kit comprising one container comprising a solution comprising a substrate being hydrolysable by a hydrolase, and a second container comprising a solution comprising alginate, a divalent cation releasing compound and a hydrolase.

Finally, the present invention provides the use of a hydrolase and a substrate being hydrolysable by the hydrolase in the preparation of an alginate hydrogel. According to one embodiment, the enzyme used according to this aspect is an esterase, such as a lipase, e.g. a triacylglycerol lipase.

According to one embodiment of this aspect, the invention provides the use of a hydrolase and a substrate in the preparation of an alginate hydrogel embedding biological material, preferably spermatozoa.

DETAILED DESCRIPTION OF THE INVENTION

The present invention provides a novel method for preparing alginate hydrogels useful for various areas of applications. In particular, the present invention provides a novel method for preparing hydrogels that in particular is useful for embedding and immobilising biological materials.

Various types of alginate may be used to prepare hydrogels according to the present invention. The ratio of guluronic acid:mannuronic acid is not critical, i.e. the type of alginate and the content of guluronic acid vs. mannuronic acid may be selected depending on the desired strength, stability, swellability, erosion characteristics etc. The use of G-rich alginates will e.g. provide for stronger, more stable hydrogels.

According to one embodiment, the alginate used to form the hydrogels is an alginate being rich in guluronic acid. The term "alginate being rich in guluronic acid" or "G-rich alginate" as used herein means alginate comprising higher amounts of guluronic acid compared to mannuronic acid in the polysaccharide polymer chain of the alginate used. Opposite, the term "M-rich alginate" or "alginate being rich in mannuronic acid" as used herein means alginate comprising higher amounts of mannuronic acid compared with guluronic acid. The term "rich" used in connection with alginates comprising either higher amounts of mannuronic acid or guluronic acid, respectively, is well known and commonly used by the skilled person, cf. e.g. Britt Iren Glaerum Svanem et al Journal of Biological Chemistry Vol 276, No 34, Aug. 24, 2001 pp 31542-31550, Sumita Jain et al Molecular Microbiology (2003) 47(4), pp 1123-1133, Marco Mancini et al Journal of Food Engineering 39 (1999) pp 369-378, Applied and Environmental Microbiology, September 1982, Vol. 44 No. 3 pp 754-756, U.S. Pat. No. 5,639,467, US application 2006/0159823, Ji Minghou (M. H. Chi) et al Hydrobiologia 116/117 (1984), pp 554-556.

Non-limiting examples of suitable alginate types to be used according to the present invention are FMC LF 10/40, FMC LF 10/60 and FMC LF 20/60 available from FMC Biopolymer AS, Drammen, Norway, A2033 from Sigma, Oslo, Norway, or Pronova UP MVG, Pronova UP LVG alginates available from e.g. NovaMatrix, Sandvika, Norway.

The function of the alginate hydrogel according to the present invention is independent of the three dimensional shape of the hydrogel formed, i.e. the alginate hydrogel may have different shapes such as e.g. a spherical or cylindrical shape. Various shapes of the alginate gel may be obtained dependent on the container used for gelling.

Also other polymers that upon being subjected to an enzyme and a substrate resulting in the release of divalent cation form hydrogels may be used according to the present invention.

According to the present invention, an enzyme, i.e. a hydrolase, together with a suitable substrate thereto, is used to initiate gelling of the alginate. The term "hydrolase" as used herein is meant to encompass a hydrolase enabling the production of $H_3O^+$ when mixing a solution comprising substrate(s) with another solution comprising the hydrolase. According to one embodiment of the invention, the hydrolase is a lipase. According to yet another embodiment of the present invention, the lipase is an acyl hydrolase, more preferably a triacylglycerol lipase, such as for example the triacylglycerol lipase isolated from the yeast Candida rugosa. A suitable lipase is available from Sigma-Aldrich Co. LLC (L1754—Type VII or L3001 Type I, CAS number 9001-62-1).

It is to be understood that any hydrolase resulting in net production of $H_3O^+$ upon to the hydrolysis of its substrate may be used according to the present invention. A hydrolase that may be used may thus be selected from the group consisting of carboxylic ester hydrolases, glycosidases, and enzymes acting on carbon-carbon bonds in ketonic substances.

Non-limiting examples of carboxylic ester hydrolases are carboxylesterase, triglycerol lipases, acetyl esterase, sterol esterase, L-arabinonolactonase, gluconolactonase, acylglycerol lipase, g-acetylglucose deacetylase, lipoprotein lipase, fatty acyl ethyl ester synthase, and diacylglycerol acylhydrolase.

Non-limiting examples of hydrolases acting on carbon-carbon bonds in ketonic substances are acylpyruvate hydrolase, and acetyl pyruvate hydrolase.

A non-limiting example of a glycosidase is α-galacturonidase.

When forming the alginate gel according to the present invention, the hydrolase and the substrate thereof are present in different solutions, which upon mixing result in initiating of the gelling process, and wherein one of the said two solutions in addition comprises alginate and a divalent cation releasing compound The sequence of the mixing, i.e. whether the solution comprising the enzyme is added to a solution comprising the substrate, or vice versa, or whether it is the solution comprising the enzyme which in addition comprises alginate and the divalent cation releasing compound, or vice versa, is not critical.

The substrate used in the forming of an alginate hydrogel according to the present invention is a substrate which upon binding to the enzyme results in the production of $H_3O^+$. The substrate may thus vary depending on the type of hydrolase used according to the present invention.

Suitable substrates according to the present invention are esters of organic acids, such as carboxylic acids.

According to one embodiment of the present invention, the substrate is a compound of formula I:

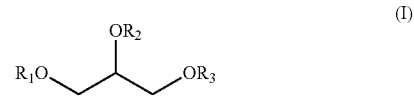

wherein $R_1$, $R_2$, and $R_3$ independently are the same or different and represents a straight or branched, substituted or non-substituted $C_1$-$C_{12}$ alkyl carbonyl chain, such as e.g. methanone, ethanone, acetone, butanone, pentanone, hexanone, heptanone, octanone, nonanone, decanone, dodecanone etc. According to one embodiment, $R_1$, $R_2$, and $R_3$ are each methanone. According to another embodiment, $R_1$, $R_2$, and $R_3$ are each ethanone. According to yet another embodiment, $R_1$, $R_2$, and $R_3$ is acetone. Substrates of the formula I is in particular useful when forming alginate hydrogels using a triacylglycerol lipase as the hydrolase according to the present invention.

Upon binding to the enzyme present in the first diluent, said ester of formula I is split into glycerol and a carboxylic acid, i.e. thus providing $H_3O^+$.

The alkyl carbonyl chain may be branched or unbranced. The alkyl carbonyl chain may furthermore be substituted or non-substituted. The skilled person will acknowledge, based on the teaching herein, that various substrate covered by the formula I may be used and may based on the teaching herein select the proper substrate to be used according to the present invention. The skilled person will thus acknowledge that the alkyl chain length may vary without affecting the ability of the enzyme to produce glycerol and a carboxylic acid of the substrate, thus resulting in the release of $H_3O^+$ ions.

According to a preferred embodiment of the present invention, the substrate is selected from the group triacetin, tripropionin and tributyrin, of the formulas:

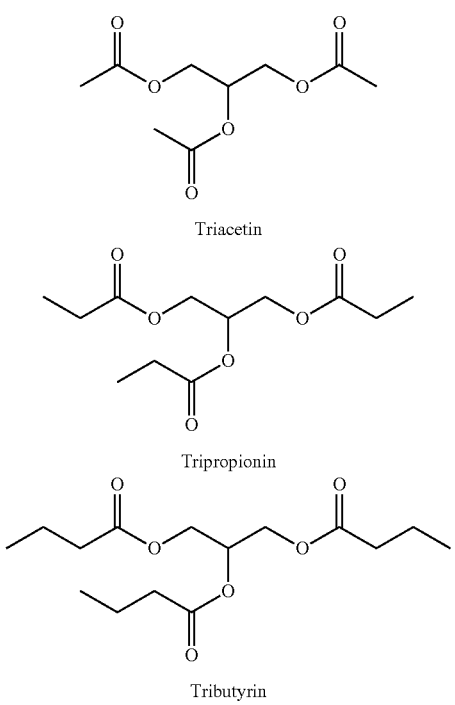

Triacetin

Tripropionin

Tributyrin

Thus, according to one embodiment, $R_1$, $R_2$, and $R_3$ represent C1-C4 alkyl carbonyl.

According to yet another embodiment of the present invention, the substrate present is selected from the group consisting of tripropionin and tributyrin.

According to the present invention, the mixing of the hydrolase and the substrate defined above results in the production of $H_3O^+$. Said $H_3O^+$ furthermore result in the release of divalent cations from the divalent cation releasing agent. The term divalent cation releasing agent is meant to encompass compounds resulting in the release of e.g. $Ca^{2+}$, $Br^{2+}$ or $Sr^{2+}$.

According to one embodiment of the present invention, the divalent cation releasing agent is a carbonate salt, such as $CaCO_3$, $BrCO_3$ or $SrCO_3$. According to a preferred embodiment, the divalent cation releasing agent is a calcium releasing agent, such as e.g. calcium carbonate.

According to one embodiment of the present invention, the method for the present invention provides for embedding various materials in the polymer matrix of the hydrogel. The term "embed" or "embedding" as used herein should be understood as immobilising a material in the alginate hydrogels of the present invention, and wherein the alginate network is present throughout the whole diameter of the hydrogel (in contrast to encapsulation wherein the hydrogel forms a wall around a liquid core not comprising a polymer network).

The term biological material is to be understood to encompass any type of biological material suitable for being immobilised or encapsulated in biocompatible hydrogels. A non-limiting list of biological material is e.g. cells for transplantation, such as e.g. insulin producing cells, hybridoma cells producing monoclonal antibodies, or spermatozoa for utilisation in artificial insemination and other reproduction technologies.

In case the material to be embedded is spermatozoa, the embedding results in that the spermatozoa are prevented from having their natural possibility of movement. The degree of immobilisation may vary dependent on the characteristics of alginate hydrogel, such as mechanical strength and ability to disintegrate e.g. after insemination in a recipient animal.

According to one preferred embodiment, the biological material to be immobilised according to the present process is spermatozoa. Spermatozoa immobilised in an alginate hydrogel prepared according to the present invention may optionally be cryopreserved for storage in liquid nitrogen. The alginate hydrogel comprising immobilized spermatozoa prepared according to the present invention may be prepared in ready-to-use insemination doses by immobilising a suitable amount of spermatozoa in the alginate hydrogel, and performing the gelling in a container, such as a straw commonly used in artificial insemination procedures having the desired size, shape and volume.

For embedding (immobilising) spermatozoa in a hydrogel according to one embodiment of the present invention, spermatozoa are diluted after harvesting in a diluent comprising either the enzyme or the substrate. Said diluted solution of spermatozoa is optionally cooled to approx. 4° C. The solution used to dilute the spermatozoa is also herein named an extender solution (cf. e.g. example 1).

According to a preferred embodiment of the invention, the spermatozoa are first diluted in an extender solution not comprising the substrate or the enzyme. The substrate or the enzyme is then added in a second dilution step wherein the extender solution then used in addition comprises either the enzyme or the substrate.

According to one embodiment, the spermatozoa is diluted a second time in an extender solution comprising the enzyme hydrolase. The so obtained solution is then mixed with a second solution comprising alginate, calcium carbonate and optionally a cryoprotectant, such as glycerol, and a substrate for the enzyme present in first solution comprising the diluted spermatozoa and the enzyme. Upon adding and mixing the two solutions, the enzyme will bind to the substrate resulting in the formation of an acid and thus an increase in the level of $H_3O^+$. The calcium carbonate acting as a buffer will prevent an increase in pH resulting in the release of $Ca^{2+}$ and the production of $CO_2$. The release of $Ca^{2+}$ results in crossbinding of the polysaccharide chains of the alginate and thus formation of the alginate hydrogel.

It is to be understood that the spermatozoa may also be diluted in an extender solution comprising the substrate being hydrolysable by the enzyme to be used in accordance with the present invention which are then mixed with a second solution comprising the enzyme, calcium carbonate and optionally a cryoprotectant.

Thus, the spermatozoa may first be diluted in an extender solution, and thereafter subjected to a second dilution by adding more of the extender solution furthermore comprising the substrate. The so obtained solution may then be mixed with a solution comprising the enzyme, alginate, calcium carbonate and optionally a cryoprotectant, such as glycerol. Upon mixing of the two solutions, the gelling is initiated.

The temperature of the solvent used to dilute the spermatozoa, and the temperature of the further steps of forming of the gel may vary dependent e.g. on the type and source of spermatozoa. The process of the present invention may thus be carried out in refrigerated conditions or at room temperature (e.g. 20-24° C.) or even at higher temperature, such as e.g. 30-35° C.

The process of the present invention renders it possible to control the rate of the gelling process by varying the amount of enzyme used. In addition, the concentration of the alginate used influences the mechanical characteristics of the hydrogel formed, and therefore also the dissolution characteristics of the hydrogel. The alginate concentration may thus vary dependent on the desired characteristics of the hydrogel, dependent on the area of application of the hydrogel. The skilled person will based on the teaching herein be able to select the suitable amount of enzyme, substrate and alginate to be used in order to obtain the desired gel strength and the desired gelling time.

For example, the use of 3 g triacylglycerol lipase per liter and 0.3-1 g substrate per 100 ml in the spermatozoa/alginate solution obtained after mixing the two solutions according to the present invention results in a gelling time of about 2-3 hr when the solution is kept at about 4° C. The amount of substrate may in addition vary according to the type of enzyme used.

In addition, the amount of acid and thus the amount of $H_3O^+$ to be produced when mixing the two solutions may be controlled by the amount of substrate present in the second diluent. It is thus possible to control both the gelling rate and the final pH of the process, which is an advantage from an industrial point of view. It provides for an improved and easier production process as one may perform the gelling whenever it is suitable from a production point of view as the gelling starts when mixing the spermatozoa diluted in an extender solution comprising either the enzyme or the substrate.

For embedding biological material, it is to be understood that solution to be mixed may in addition comprise compounds useful for example for preservative purposes, such as e.g. antibiotics, extenders, antioxidants, buffers, etc., see WO 2008/004890.

The concentration of biological material, e.g. living cells, embedded in the alginate hydrogels according to the present invention may vary depending on the type/source of the material. In case of embedding spermatozoa, the concentration may further vary depending on the breed, recipient animal, insemination techniques, the presence of additional compounds (e.g. for preservative purposes) etc., see e.g. WO 2008/004890.

Although the present invention is specifically useful for embedding biological material in form of cells or tissues in an alginate gel, it is to be understood that alginate gels prepared according to the present invention also have a range of other applications, including embedding or immobilising of other objects than biological material, and also applications involving the hydrogels per se. The present invention is thus not to be construed as limited to the applications specifically disclosed in the examples in the specification.

Thus, other objects of interest may also be embedded in an alginate hydrogel prepared according to the present invention. The term "object to be embedded in the alginate hydrogel" used herein is meant to encompass any material which is suitable for being immobilised in a hydrogel. For example, in case the alginate hydrogel according to the present invention is to be used as a controlled release system, the object to be embedded may be a pharmaceutical active ingredient. For example, alginate gels prepared according to the present invention may be used as a controlled release or sustained release delivery system for a range of compounds, such as pharmaceutically active compounds, see e.g. WO98/46211, U.S. Pat. No. 4,695,463, U.S. Pat. No. 6,656,508, which are incorporated herein by reference. A non-limiting group of pharmaceutically active ingredients to be embedded in an alginate hydrogel according to the present invention are e.g. recombinant or naturally occurring proteins or polypeptides, natural or synthetic or semi-synthetic compounds, such as growth factors, hormones, antibodies, interferones, interleukins, etc. The alginate hydrogels according to the present invention may also have utilities within the food industry, e.g. for the embedding of nutritive.

The hydrogels prepared according to the present invention may also be used as such for other industrial purposes, both in pharmaceutical industry or cosmetic industry (e.g. as a thickening agent, in wound dressings, in dental health products and methods), or in the human and animal food industry (e.g. in preparation of restructured food, as thickening agent, etc).

The present invention provides advantages compared with the prior art. For example, when using the technique described in U.S. Pat. No. 6,497,902, the reaction rate as well as the amount of acid produced can be influenced by changing the concentration of GDL. Changes in the GDL-concentration will however simultaneously also affect the amount of acid produced and thus the final pH in the gel. The preparation of an alginate hydrogel using an enzyme and substrate hydrolysable by said enzyme to initiate gelling allows a significantly better control of reaction rates and the amount of acid produced (the pH in the gel) as the reaction rate and the final pH can be individually controlled by changing the concentration of enzyme and substrate, respectively.

According to yet another aspect of the present invention, the present invention provides an alginate hydrogel kit comprising a container comprising a hydrolase, and another container comprising a substrate being hydrolysable by the hydrolase.

The kit according to the present invention may also contain other compounds necessary for casting an alginate hydrogel according to the present invention. Thus, the kit may also comprise alginate and a divalent cation releasing compound. Said compounds may be contained in the container comprising the hydrolase, in the container comprising the substrate being hydrolysable by the said hydrolase, or they may be contained in separate container(s).

The containers may also comprise other compounds of particular interest depending on the use of the alginate hydrogel to be casted using the kit of the present invention.

For example, in case the kit is to be used for casting gels comprising biological material, such as cellular material, e.g. spermatozoa, and wherein the resulting alginate hydrogel is to be further subjected to cryopreservation, the kit may furthermore contain a cryoprotectant such as e.g. glycerol, ethylene glycol, methanol, DMA, DMSO, propylene glycol, trehalose, glucose. Said cryoprotectant(s) may be contained in the container comprising the hydrolase, in the container comprising the substrate being hydrolysable by the said hydrolase, or they may be contained in separate container(s).

The kit may also comprise other compounds useful for preservative purposes, such as e.g. antibiotics, extenders, antioxidants, buffers, etc. known to the skilled person in the art, see e.g. WO 2008/004890.

For illustration purposes, the following examples are given. It is to be understood that the examples below are not to be construed as limiting the scope of the present invention. The foregoing description of various embodiments of the present invention reveals the general nature of the invention and the skilled person will by applying the general knowledge within the area of hydrogels, readily modify and/or adapt the method of the present invention, without undue experimentation, without departing from the general concept of the present invention and the scope of the enclosed claims. Such adaptations or modifications are thus intended to be within the meaning of a range of equivalents of the disclosed embodiments, based on the teaching and guidance presented herein. It is to be understood that the terminology used herein is for the purpose of description and not of limitation. Thus, the terminology of the present specification is to be interpreted by the skilled person in light of the teachings and guidance presented herein, in combination with the knowledge of the skilled person.

Example 1: Immobilization of Bovine Spermatozoa

Materials and Methods
Materials

The following chemicals were used: trizma hydrochloride and EDTA from Sigma (St. Luis, USA), $NaHCO_3$, NaCl, glycerol (>99%), sodium citrate and sodium pyruvate from Riedel de Haën (Seelze, Germany), fructose and glucose monohydrate from Norsk Medisinaldepot (Oslo, Norway), calcium carbonate from KSL staubtechnik gmbh (Lauingen, Germany) and sodium alginate (PROTANAL LF 10/60) from FMC Biopolymer A/S (Drammen, Norway).

Source of Spermatozoa

Bovine spermatozoa were collected at the Geno facilities at Hallsteingård in Trondheim and Store Ree in Stange, Norway.

Buffer Solutions

The following extender solutions were used: Extender for first dilution of spermatozoa: 1.45 g $l^{-1}$ Trizma hydrochloride glucose, 0.4 g $l^{-1}$ sodium citrate, 1 g $l^{-1}$ fructose, 0.22 g $l^{-1}$ sodium pyruvate and 200 ml $l^{-1}$ egg yolk. The pH of the solution was adjusted to 6.4 by addition of NaOH.

Extender solution for secondary dilution of spermatozoa: 4 g $l^{-1}$ calcium carbonate (unless otherwise stated), 54 g $l^{-1}$ fructose, 170 g $l^{-1}$ glycerol and 24 g $l^{-1}$ LF10/60 sodium alginate. Both extenders contain standard antibiotic cocktail giving at least the final concentration required in EU dir 88/407. Modified IVT: 3 g $l^{-1}$ glucose, 20 g $l^{-1}$ sodium citrate, 2.1 g $l^{-1}$ $NaHCO_3$, 1.16 g $l^{-1}$ NaCl, 3 g $l^{-1}$ EDTA, pH 7.35. The extender solutions were added either enzyme (Sigma L1754) or substrate as specified below.

Dilution, Immobilization and Cryoconservation of Bull Spermatozoa

Bovine spermatozoa were harvested at the Geno facilities and diluted as described below: Immediately after harvesting, the spermatozoa were diluted to a concentration of $219 \times 10^6$ cells per ml in the extender solution for a first dilution. This solution was then immediately mixed with an equal volume of extender for further dilution where said extender now comprised either enzyme or substrate. The resulting solution containing diluted spermatozoa was then cooled to 4° C.

After cooling to 4° C., the solution was mixed with an equal volume of the extender solution for a third dilution where said extender now comprised either substrate (triacetin, tripropionin or of tributyrin) if the diluted spermatozoa from the previous step comprised the enzyme or enzyme if the diluted spermatozoa from the previous step comprised the substrate. In addition, the extender now comprised calcium carbonate as a divalent cation releasing compound and alginate. The resulting solutions was then transferred to insemination straws and equilibrated at 4° C. for approximately 3 hours. The insemination straws was then transferred to a $N_2$-freezer and frozen according to standard procedures for bull semen.

Assessment of Motility

The motility of the spermatozoa was assessed through a microscopic evaluation. Frozen semen straws were thawed by holding the straws in water bath at 37° C. for 30 seconds. Prior to measurement the alginate gel was liquefied in modified IVT solution. The content of an insemination straw was added to 0.9 ml of IVT solution and shaken carefully on a tube-tumbler for approximately 10 minutes. Prior to assessment of motility, the tubes were preheated for minimum 15 minutes in a heat-block at 37° C. Approximately 3 μl of the solution was added to a preheated microscope slide and immediately inspected using a light microscope. The number of motile spermatozoa in each sample was estimated to the nearest 5% interval. If practically possible, the operator was unaware of the sample identity during the assessment.

Results a) Immobilization of Bovine spermatozoa using triacetin as a substrate Spermatozoa was collected and diluted according to the procedures described above. The extender solution for second dilution was added enzyme (Sigma L1754) to a concentration of 6 g $l^{-1}$ in the final solution containing spermatozoa. The extender solution for third dilution contained 8 g $l^{-1}$ calcium carbonate and was added triacetin to a concentration of 0.5 g/100 ml. Approximately 4 hours after the secondary dilution a gel was formed immobilizing the spermatozoa. After approximately 24 hours of storage at 4° C. the gel was liquefied and the motility of the immobilized spermatozoa was assessed. Approximately 60% of the spermatozoa were motile at that time.

b) Immobilization of Bovine spermatozoa using tripropionin as a substrate Spermatozoa were collected, diluted, immobilized and cryoconserved according to the procedures described above. The extender solution for the second dilution was added enzyme (Sigma L1754) to a concentration of 6 g $l^{-1}$ in the final solution containing diluted spermatozoa. The extender solution for third dilution contained 4 g $l^{-1}$ calcium carbonate and was added tripropionin to a concentration of 0.30 g/100 ml. Approximately 3 hours after the secondary dilution a gel was formed and the straws containing the immobilized spermatozoa were frozen. The semen straws were stored in liquid $N_2$ for several days until thawing and assessment of motility. Approximately 60% of the spermatozoa were motile after thawing and liquefying of the gel.

c) Immobilization of Bovine spermatozoa using tripropionin as a substrate Spermatozoa were collected, diluted, immobilized and cryoconserved according to the procedures described above. The extender solution for the second dilution was added tripropionin to a concentration of 0.30 g/100 ml in the final solution containing diluted spermatozoa. The extender solution for the third dilution contained 4 g $l^{-1}$ calcium carbonate and was added enzyme Sigma L1754 to a concentration of 6 g $l^{-1}$. Approximately 2 hours after the secondary dilution a gel was formed. After approximately 24 hours of storage at 4° C. the gel was liquefied and the motility of the immobilized spermatozoa was assessed. Approximately 60% of the spermatozoa were motile at that time.

d) Immobilization of Bovine spermatozoa using tributyrin as a substrate Spermatozoa were collected, diluted, immobilized and cryoconserved according to the procedures described above. The extender solution for the second dilution was added enzyme (Sigma L1754) to a concentration of 6 g $l^{-1}$ in the final solution containing diluted spermatozoa. The extender solution for the third dilution contained 4 g $l^{-1}$ calcium carbonate and was added tributyrin to a concentration of 0.35 g/100 ml. Approximately 3 hours after the secondary dilution a gel was formed and the straws containing the immobilized spermatozoa were frozen. The semen straws were stored in liquid $N_2$ for several days until thawing and assessment of motility. Approximately 60% of the spermatozoa were motile after thawing and liquefying of the gel.

Example 2: Controlled Preparation of Calcium Alginate Gel Using Lipase Enzymes and Triacetin or Trioctanoate Substrates Materials and Methods
Materials Sodium alginate (PROTANAL LF 10/60) from FMC Biopolymer A/S (Drammen, Norway), enzymes L3001 and L1754 from Sigma (St. Luis, USA), Triacetin and trioctanoate from Sigma (St. Luis, USA), calcium carbonate from KSL staubtechnik gmbh (Lauingen, Germany)

Solutions

The following solutions were used. Solution L1.1: $10 \text{ g l}^{-1}$ solution of L3001 enzyme in distilled water, Solution L1.2: $0.2 \text{ g l}^{-1}$ triacetin in distilled water. Solution L2.1: $4 \text{ g l}^{-1}$ calcium carbonate, $24 \text{ g l}^{-1}$ LF10/60 sodium alginate and $0.1 \text{ g l}^{-1}$ triacetin in distilled water. Solution L2.2: $4 \text{ g l}^{-1}$ calcium carbonate, $24 \text{ g l}^{-1}$ LF10/60 sodium alginate and $0.2 \text{ g l}^{-1}$ triacetin in distilled water. Solution L2.3: $4 \text{ g l}^{-1}$ calcium carbonate, $24 \text{ g l}^{-1}$ LF10/60 sodium alginate and $0.3 \text{ g l}^{-1}$ triacetin in distilled water. Solution L2.4: $4 \text{ g l}^{-1}$ calcium carbonate, $24 \text{ g l}^{-1}$ LF10/60 sodium alginate and $10 \text{ g l}^{-1}$ L3001 enzyme in distilled water. Solution L2.5: $4 \text{ g l}^{-1}$ calcium carbonate, $24 \text{ g l}^{-1}$ LF10/60 sodium alginate and $0.3 \text{ g l}^{-1}$ trioctanoate in distilled water.

Initiation of Gelling

Gelling was initialized by mixing of one of the L1-solutions with an equal volume of one of the L2-solutions. The solutions were mixed according to table 1.

TABLE 1

Experimental trials with gelling using enzyme L3001 and triacetin substrate. The combinations of solutions investigated are shown in the table as well as concentrations of enzyme and triacetin substrate used.

| Trial | Solutions | Concentrations |
| --- | --- | --- |
| 1 | L1.1 + L2.1 | 10 g l$^{-1}$ enzyme L3001, 0.1 g l$^{-1}$ triacetin |
| 2 | L1.1 + L2.2 | 10 g l$^{-1}$ enzyme L3001, 0.2 g l$^{-1}$ triacetin |
| 3 | L1.1 + L2.3 | 10 g l$^{-1}$ enzyme L3001, 0.3 g l$^{-1}$ triacetin |
| 4 | L1.2 + L2.4 | 0.2 g l$^{-1}$ triacetin, 10 g l$^{-1}$ enzyme L3001 |
| 5 | L1.2 + L2.2 | 0.2 g l$^{-1}$ triacetin, 0.2 g l$^{-1}$ triacetin (no enzyme added) |
| 6 | L1.3 + L2.5 | 10 g l$^{-1}$ enzyme L1754, 0.4 g l$^{-1}$ trioctanoate |

All solutions were at ambient temperature before mixing, and the solutions were left at ambient temperature for gelling. The time course of the gelling reaction was followed by visual inspection of the solutions.

Results

The enzymes L3001 (lipase from wheat germ) and L1754 (lipase from *Candida rugosa*) and the substrates triacetin and trioctanoate were used for controlled gelling of sodium alginate solutions. Solutions of enzyme and substrate were prepared and mixed according to table 1. The reaction between enzyme and substrate produces $H_3O^+$-ions that react with suspended calcium carbonate in the solutions. This reaction releases calcium ions which interact with alginate polymer chains in the solution and a gel is formed. The observed times before a gel were formed in the experimental trials are shown in table 2. No gel was formed in experimental trial 5 in which no enzyme were added. The results show that the reaction time is dependent on both type of substrate and enzyme selected as well as on the concentrations of enzyme and substrate used.

TABLE 2

Observed time before gelling occurs after mixing solutions containing enzymes (Sigma L3001 or L1754) and/or substrate (triacetin or trioctanoate).

| Trial | Solutions | Time for gel formation (h:m) |
| --- | --- | --- |
| 1 | L1.1 + L2.1 | 2:00 |
| 2 | L1.1 + L2.2 | 1:50 |
| 3 | L1.1 + L2.3 | 1:30 |
| 4 | L1.2 + L2.4 | 1:50 |
| 5 | L1.2 + L2.2 | No gel was formed |
| 6 | L1.3 + L2.5 | 0:30 |

The invention claimed is:
1. An alginate hydrogel prepared by
mixing a first solution comprising a hydrolase with a second solution comprising a substrate hydrolysable by the hydrolase, wherein the first solution comprising said hydrolase or the second solution comprising said substrate comprises alginate and a divalent cation releasing compound, wherein the mixing causes hydrolysis of the substrate by the hydrolase to produce $H_3O^+$ and reaction of the $H_3O^+$ with the divalent cation releasing compound to release divalent cations which initiate gelling of the mixture, and
gelling the mixture to provide the alginate hydrogel, wherein the first solution or the second solution comprises a biological material, and after gelling, the biological material is embedded in the hydrogel, wherein the biological material-comprises spermatoazoa.

* * * * *